US010709801B2

(12) United States Patent
Medina-Kauwe

(10) Patent No.: US 10,709,801 B2
(45) Date of Patent: *Jul. 14, 2020

(54) TARGETING CORROLES FOR TUMOR TOXICITY AND MRI

(71) Applicant: Cedars-Sinai Medical Center, Los Angeles, CA (US)

(72) Inventor: Lali K. Medina-Kauwe, Porter Ranch, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/624,228

(22) Filed: Jun. 15, 2017

(65) Prior Publication Data
US 2017/0281802 A1 Oct. 5, 2017

Related U.S. Application Data

(63) Continuation of application No. 14/272,610, filed on May 8, 2014, now Pat. No. 9,757,386.

(60) Provisional application No. 61/821,106, filed on May 8, 2013.

(51) Int. Cl.
| *A61K 49/10* | (2006.01) |
| *A61K 31/555* | (2006.01) |
| *A61K 49/18* | (2006.01) |
| *A61K 33/24* | (2019.01) |
| *A61K 33/26* | (2006.01) |
| *A61K 33/32* | (2006.01) |
| *A61K 47/64* | (2017.01) |
| *A61K 9/16* | (2006.01) |
| *A61K 9/51* | (2006.01) |

(52) U.S. Cl.
CPC .............. *A61K 49/106* (2013.01); *A61K 9/16* (2013.01); *A61K 31/555* (2013.01); *A61K 33/24* (2013.01); *A61K 33/26* (2013.01); *A61K 33/32* (2013.01); *A61K 47/642* (2017.08); *A61K 49/1818* (2013.01); *A61K 9/5115* (2013.01)

(58) Field of Classification Search
CPC .. A61K 31/555; A61K 49/106; A61K 9/5115; A61K 47/48; C12N 15/00
See application file for complete search history.

(56) References Cited

U.S. PATENT DOCUMENTS

| 5,559,099 A | 9/1996 | Wickham et al. |
| 6,939,963 B2 | 9/2005 | Gross et al. |
| 9,078,927 B2 | 7/2015 | Medina-Kauwe |
| 9,757,386 B2 | 9/2017 | Medina-Kauwe |
| 10,391,180 B2 | 8/2019 | Medina-Kauwe |
| 2004/0180872 A1 | 9/2004 | Gross et al. |
| 2010/0331273 A1 | 12/2010 | Medina-Kauwe |
| 2011/0318338 A1 | 12/2011 | Donald |
| 2012/0004181 A1 | 1/2012 | Medina-Kauwe |
| 2012/0071540 A1 | 3/2012 | Lu et al. |
| 2013/0065778 A1 | 3/2013 | Weidhaas |
| 2015/0240231 A1 | 8/2015 | Medina-Kauwe |
| 2016/0008481 A1 | 1/2016 | Medina-Kauwe |
| 2016/0060316 A1 | 3/2016 | Medina-Kauwe |
| 2016/0331840 A1 | 11/2016 | Medina-Kauwe |
| 2018/0066033 A1 | 3/2018 | Medina-Kauwe |
| 2018/0298376 A1 | 10/2018 | Medina-Kauwe |
| 2019/0175747 A1 | 6/2019 | Medina-Kauwe |

FOREIGN PATENT DOCUMENTS

| WO | WO-2002/094318 A1 | 11/2002 |
| WO | WO-2003/004021 A1 | 1/2003 |
| WO | WO-2009/027965 A1 | 3/2009 |
| WO | WO-2009/095923 A2 | 8/2009 |
| WO | WO-2009/095923 A3 | 8/2009 |

OTHER PUBLICATIONS

Agadjanian et al., PNAS, vol. 106, No. 15, 6100-6105, Apr. 14, 2009.*
Hwang et al., PLoS ONE, vol. 7, Issue 4, e34464, 1-9, Apr. 2012.*
Agadjanian et al. (Feb. 2006). "Specific Delivery of Corroles to Cells via Noncovalent Conjugates with Viral Proteins," *Pharmaceutical Research*, 23(2):367-377.
Agadjanian, H. et al. (Apr. 14-18, 2007). "Modified Viral Capsid Protein Mediates Non-Viral Targeting of Unique Non-Covalent Drug Conjugates to HER2+ Breast Cancer Cells," *Proceedings of the AACR Annual Meeting* 48:357, Abstract # 1505 (Abstract Only), 2 pages.
Agadjanian et al. (Apr. 2008). "Corrole Conjugates: A Unique Approach to Tumor Targeting," *Proceedings of the American Association for Cancer Research Annual Meeting*, 49:549-550. Meeting: 99th Annual Meeting of the American-Association-for-Cancer-Research. San Diego, CA, USA. Apr. 12-16, 2008. Abstract 2328.
Agadjanian, H. et al. (Mar. 2012). "Chemotherapy Targeting by DNA Capture in Viral Protein Particles," *Nanomedicine (Lond)* 7(3):335-352, author manuscript, pp. 1-26).
Albanell, J. et al. (1999). "Trastuzumab, A Humanized Anti-HER2 Monoclonal Antibody, for the Treatment of Breast Cancer," *Drugs of Today* 35(12):931 (Abstract Only).
Blumenfeld, C.M. et al. (Nov. 2014). "Cellular Uptake and Cytotoxicity of a Near-IR Fluorescent Corrole-TiO$_2$ Nanoconjugate," *Journal of Inorganic Biochemistry* 140:39-44.

(Continued)

*Primary Examiner* — Robert S Cabral
(74) *Attorney, Agent, or Firm* — Morrison & Foerster LLP

(57) ABSTRACT

Disclosed herein are compositions comprising a targeted corrole nanoparticle; and an acceptable excipient. Also disclosed are compositions comprising a targeted corrole nanoparticle; and an acceptable carrier. Further, disclosed herein are methods of imaging a condition in a subject, comprising providing a composition comprising a targeted corrole nanoparticle; administering an effective amount of the targeted corrole nanoparticle to the subject; and imaging the condition in the subject. In addition, disclosed herein are methods of treating cancer in a subject, comprising providing a composition comprising a targeted corrole nanoparticle; and administering a therapeutically effective dosage of the targeted corrole nanoparticle to the subject.

12 Claims, 3 Drawing Sheets

(56) References Cited

OTHER PUBLICATIONS

Hwang, J.Y. et al. (2011). "A Mechanistic Study of Tumor-Targeted Corrole Toxicity," *Mol. Pharmaceuticals* 8:2233-2243.
Hwang, J.Y. et al. (Jun. 2011). "Ratiometric Spectral Imaging for Fast Tumor Detection and Chemotherapy Monitoring In Vivo," *Journal of Biomedical Optics* 16(6):066007-1-066007-6.
Hwang, J.Y. et al. (2011) "Multimode Optical Imaging for Translational Chemotherapy: In Vivo tumor Detection and Delineation by Targeted Gallium Corroles," *Proc. of SPIE.* 7902:79020F:1-8.
Hwang, J.Y. et al. (2011) "Investigating the Photosensitizer-Potential of Targeted Gallium Corrole Using Multimode Optical Imaging," *Proc. of SPIE*, 7886:78860M:1-6.
Hwang, J.Y. et al. (Jan. 2012). "Investigating Photoexcitation-Induced Mitochondrial Damage by Chemotherapeutic Corroles Using Multimode Optical Imaging," *Journal of Biomedical Optics* 17(1): 015003-1-015003-11.
Hwang, J.Y. et al. (2012). "Photoexcitation of Tumor-Targeted Corroles Induces Singlet Oxygen-Mediated Augmentation of Cytotoxicity," *Journal of Controlled Release* 163:368-373.
Kanamori et al. (2010). "Neuroprotection Against Superoxide Anion Radical by Metallocorroles in Cellular and Murine Models of Optic Neuropathy," *J. of Neurochemistry* 114:488-498.
Kedes, L.H. et al. (Aug. 2002). "A Novel Gene Delivery System Targeted to Breast Cancer Cells," Report DAMD17-99-1-9378 prepared for U.S. Army medical research, (38 pages).
Kochut, A. et al. (2013). "Bacterial Invasion Factors: Tools for Crossing Biological Barriers and Drug Delivery?" *European Journal of Pharmaceuticals and Biopharmaceuticals*, (2013), 84(2):242-250.
Kupershmidt et al. (2010). "Metallocorroles As Cytoprotective Agents Against Oxidative and Nitrative Stress in Cellular Models of Neurodegeneration," *J. of Neurochemistry* 113:363-373.
Lee, T. (2010). "In Vivo Imaging with a Cell-Permeable Porphyrin-Based MRI Contrast Agent," *Chemistry & Biology* 17:665-673.
Mahammed, A. (2005). "Albumin-Conjugated Corrole Metal Complexes: Extremely Simple Yet Very Efficient Biomimetic Oxidation Systems," *J. Am. Chem. Soc.* 127:2883-2887.
Medina-Kauwe, L.K.et al. (Aug. 24-29, 1997). "A Novel Gene Delivery System for Cell-Specific Targeting," *FASEB Journal* 11(9):A862, Meeting: 17th International Congress of Biochemistry and Molecular Biology in conjunction with the Annual Meeting of the American Society for Biochemistry and Molecular Biology, San Francisco, CA.
Medina-Kauwe et al. (2001). "3PO, a Novel Non-Viral Gene Delivery System Using Engineered Ad5 Penton Proteins," *Gene Therapy* 8:795-803.
Medina-Kauwe, L.K. et al. "Nonviral Gene Delivery to Human Breast Cancer Cells by Targeted Ad5 Penton Proteins," *Gene Therapy* (2001), 8:1753-1761.
Medina-Kauwe, L.K. et al. (Nov. 2002). "Ad5 Capsid Protein Uptake and Trafficking in HeLa Cells," *Molecular Biology of the Cell*, 13(Supplement):541a-542a. Meeting: 42nd Annual Meeting of the American Society for Cell Biology. San Francisco, CA, USA. American Society for Cell Biology.
Medina-Kauwe, L.K. (Nov. 14, 2003). "Endocytosis of Adenovirus and Adenovirus Capsid Proteins," *Adv. Drug Delivery Rev.* 55(11):1485-1496.
Medina-Kauwe, L.K. (2003). "Heregulin-Targeted Protein Uptake for Breast Cancer," NCI: 1R01CA102126-01, Abstract Only, 4 pages.
Medina-Kauwe, L.K. (2004). "Heregulin-Targeted Protein Uptake for Breast Cancer," NCI: 5R01CA102126-02, Abstract Only, 4 pages.
Medina-Kauwe, L.K. (2005). "Heregulin-Targeted Protein Uptake for Breast Cancer," NCI: 5R01CA102126-03, Abstract Only, 4 pages.
Medina-Kauwe, L.K. (2006). "Heregulin-Targeted Protein Uptake for Breast Cancer," NCI: 5R01CA102126-04, Abstract Only, 4 pages.

Medina-Kauwe, L.K. (2005). "Introduction to the Special Issue: Traveling the Intracellular Highway to Gene Therapy," *Gene Therapy* 12:863-864.
Medina-Kauwe, L.K. et al. (2005). "Intracellular Trafficking of Nonviral Vectors," *Gene Ther.* 12:1734-1751.
Medina-Kauwe, L.K. (2006). "Non-Viral Mediated Gene Delivery for Therapeutic Applications," *Gene Therapy for Neurological Disorders*, 115-140 (Chapter 8).
Medina-Kauwe, L.K. (2007). "A Novel Targeted Therapeutic Using Viral Capsid Protein," NCI: 1R21CA116014-01A2, Abstract Only, 4 pages.
Medina-Kauwe, L.K. (2008). "A Novel Targeted Therapeutic Using Viral Capsid Protein," NCI: 5R21CA116014-02, Abstract Only, 4 pages.
Medina-Kauwe, L.K. (2009). "Protein-DNA Drug Carriers for Tumor Targeting," NCI: 1R01CA129822-01A2, Abstract Only, 4 pages.
Medina-Kauwe, L.K. (2010). "Protein-DNA Drug Carriers for Tumor Targeting," NCI: 5R01CA129822-02, Abstract Only, 4 pages.
Medina-Kauwe, L.K. (2011). "Protein-DNA Drug Carriers for Tumor Targeting," NCI: 4R01CA129822-03, Abstract Only, 4 pages.
Medina-Kauwe, L.K. (2012). "Protein-DNA Drug Carriers for Tumor Targeting," NCI: 5R01CA129822-04, Abstract Only, 4 pages.
Medina-Kauwe, L.K. (2010). "Tumor Targeted Corroles for Detection and Intervention," NCI: 1R01CA140995-01A1, Abstract Only, 5 pages.
Medina-Kauwe, L.K. (2011). "Tumor Targeted Corroles for Detection and Intervention," NCI:5R01CA140995-02, Abstract Only, 5 pages.
Medina-Kauwe, L.K. (2012). "Tumor Targeted Corroles for Detection and Intervention," NCI:5R01CA140995-03, Abstract Only, 5 pages.
Medina-Kauwe, L.K. (2013). "Tumor Targeted Corroles for Detection and Intervention," NCI: 5R01CA140995-04, Abstract Only, 5 pages.
Medina-Kauwe, L.K. (2014). "Tumor Targeted Corroles for Detection and Intervention," NCI: 5R01CA140995-05, Abstract Only, 5 pages.
Medina-Kauwe, L.K. (Feb. 2013). "Development of Adenovirus Capsid Proteins for Targeted Therapeutic Delivery," *Ther Deliv.* 4(2):267-277.
Pan, D. et al. (2011) "Manganese-Based MRI Contrast Agents: Past, Present, and Future," *Tetrahedron* 67:8431-8444.
Rentsendorj et al. (May 2006, e-pub. Feb. 16, 2016). "Typical and Atypical Trafficking Pathways of Ad5 Penton Base Recombinant Protein: Implications for Gene Transfer," *Gene Ther.* 13(10):821-836.
Sims et al. (Feb. 1, 2013). "Abstract A101: Treating Trastuzumab-Resistant HER2+ Breast Cancers with a HER3-Targeted Nanoparticle," *Cancer Research*, 73(3 Supp), Meeting: AACR Special Conference on Tumor Invasion and Metastasis 2013. San Diego, CA, United States. Jan. 20, 2013-Jan. 23, 2013.
Sims, J.D. et al. (2015)., A Corrole Nanobiologic Elicits Tissue-Activated MRI Contrast Enhancement and Tumor-Targeted Toxicity, *J. Control Research* 217:92-101.
Taqavi et al. (Aug. 17, 2008). "Developing Macrocyclic Fluorescent Probes for In Vivo Molecular Imaging," *Abstracts of Papers American Chemical Society*, 236:654-INOR. Meeting: 236th National Meeting of the American-Chemical-Society. Philadelphia, PA, USA. Aug. 17-21, 2008.
Wang, Y. et al., "Different Mechanisms for Resistance to Trastuzumab Versus Lapatinib in HER2-Positive Breast Cancer-Role of Estrogen Receptor and HER2 Reactivation," *Breast Cancer Res.*, (2011), 13(6):R121.
International Preliminary Report on Patentability dated Nov. 10, 2015, for PCT/US2014/037234, filed on May 8, 2014, 6 pages.
U.S. Appl. No. 15/703,323, filed Sep. 13, 2017, for Medina-Kauwe et al. (Copy not attached).
Lim, P. et al. (Feb. 20, 2012, e-pub. Dec. 20, 2011). "Differential Cytostatic and Cytotoxic Action of Metallocorroles Against Human Cancer Cells: Potential Platforms for Anticancer Drug Development," *Chemical Research in Toxicology*, 25(2):400-409.

(56) References Cited

OTHER PUBLICATIONS

MRI (1989). "Igaku-no-ayumi," *Journal of Clinical and Experimental Medicine* 148(5):317-320 (English translation of Abstract).

Strijkers, G. et al. (May 1, 2007) "MRI Contrast Agents: Current Status and Future Perspectives," *Anti-Cancer Agents in Medicinal Chemistry* 7(3):291-305.

Allen, C.M. et al. (Oct. 1999). "Photodynamic Therapy: Tumor Targeting With Adenoviral Proteins," Photochem. Photobiol. 70(4):512-523.

Han, X. et al. (Oct. 1995). "Ligand-Directed Retroviral Targeting of Human Breast Cancer Cells," Proc. Natl. Acad. Sci. USA 92:9747-9751.

U.S. Appl. No. 16/197,240, filed Nov. 20, 2018, for Medina-Kauwe et al. (U.S. Patent Application is not submitted herewith pursuant to the waiver of 37 C.F.R. §1.98(a)(2)(iii) issued by the Office on Sep. 21, 2004.

U.S. Appl. No. 16/510,517, filed Jul. 12, 2019, for Medina-Kauwe et al. (U.S. Patent Application is not submitted herewith pursuant to the waiver of 37 C.F.R. §1.98(a)(2)(iii) issued by the Office on Sep. 21, 2004.

\* cited by examiner

Figure 2. Assembly of HerMn.

TARGETING CORROLES FOR TUMOR TOXICITY AND MRI

CROSS-REFERENCE TO RELATED APPLICATIONS

This present application is a continuation application of U.S. patent application Ser. No. 14/272,610, filed May 8, 2014, which claims the benefit of priority to the U.S. Provisional Application Ser. No. 61/821,106, filed May 8, 2013, the disclosure of which are herein incorporated by reference in their entirety, including the drawings.

STATEMENT REGARDING FEDERALLY-SPONSORED RESEARCH

This invention was made with government support under Grant No. CA 129822, Grant No. CA 140995, and Grant No. TR000124 awarded by National Institutes of Health. The government has certain rights in the invention.

FIELD OF INVENTION

This invention relates to the treatment of cancer and imaging techniques.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Whereas cancer treatment by porphyrins and related macrocyclic compounds has been investigated extensively for many decades, the therapeutic potential of corroles has only recently been disclosed. Sulfonated corroles are water soluble (amphipolar) macrocyclic compounds, whose Fe(III) and Mn(III) complexes are very active catalysts for decomposition of reactive oxygen and nitrogen species involved in a variety of relevant diseases. Also noteworthy is the finding that Ga(III) and Al(III) derivatives are intensely fluorescent at relatively long wavelengths. While these metal complexes are capable of undergoing endocytosis via co-uptake with, or noncovalent attachment to, serum proteins in vitro and in vivo, they are unable to penetrate cell membranes without facilitation by membrane-lytic molecules. Hence, toxic corroles, such as the Ga(III) derivative, are safe at pharmacologic doses but can kill cells when allowed to breach into the cytosol.

SUMMARY OF THE INVENTION

Disclosed herein are compositions comprising a targeted corrole nanoparticle; and an acceptable excipient. Also disclosed are compositions comprising a targeted corrole nanoparticle; and an acceptable carrier. Further, disclosed herein are methods of imaging a condition in a subject, comprising providing a composition comprising a targeted corrole nanoparticle; administering an effective amount of the targeted corrole nanoparticle to the subject; and imaging the condition in the subject. In addition, disclosed herein are methods of treating cancer in a subject, comprising providing a composition comprising a targeted corrole nanoparticle; and administering a therapeutically effective dosage of the targeted corrole nanoparticle to the subject.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
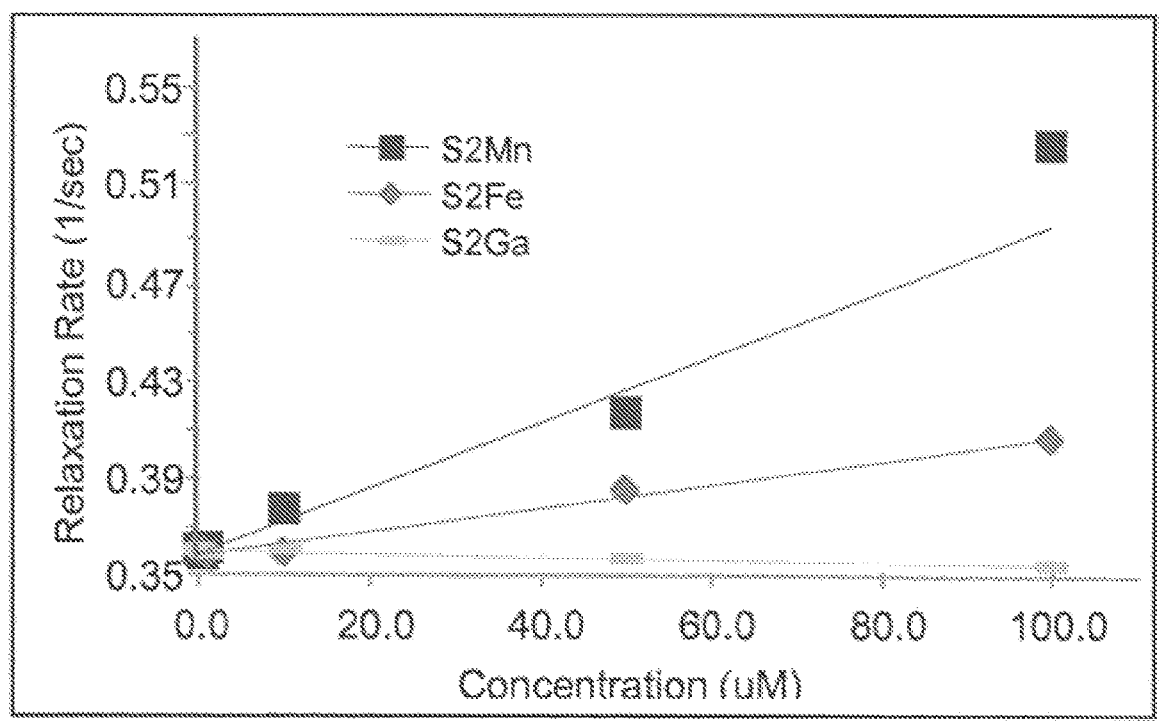
FIG. 1 depicts, in accordance with an embodiment herein, measuring T1 relaxation time of Mn, Fe, and Ga corroles. Different concentrations of each corrole were prepared and measured in situ (in a microfuge tube) for T1 relaxation time.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning; A Laboratory Manual* 3rd ed., Cold Spring Harbor Laboratory Press (Cold Spring Harbor, N.Y. 2001), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, "treatment" or "treating" should be understood to include any indicia of success in the treatment, alleviation or amelioration of an injury, pathology or condition. This may include parameters such as abatement, remission, diminishing of symptoms, slowing in the rate of degeneration or decline, making the final point of degeneration less debilitating; improving a patient's physical or mental well-being; or, preventing the onset of disease.

In one embodiment, disclosed herein are tumor-targeted protein-based nanoparticles that are capable of both imaging and tumor detection, as well as tumor treatment. In one embodiment, the nanoparticle is the combination of metallated corroles, specifically manganese (Mn), iron (Fe), or gallium (Ga), and HerPBK10 molecules, resulting in a HerMn, HerFe, or HerGa nanoparticle, respectively. As further disclosed herein, studies demonstrated that HerGa only allowed tumor detection when tumors were localized within several centimeters under the skin, and that thus usage of HerGa for tumor detection may require more advanced imaging methodologies than MRI. Studies also demonstrated that HerMn exhibited greater potential as an imaging agent for MRI as compared to HerFe. Additional studies focused on HerMn, finding that in addition to being a suitable imaging agent for MRI, HerMn exhibited significant inhibition of tumor growth in vivo.

HerPBK10 is defined and described in the art, for example in U.S. Patent Application Publication No. US 2012/0004181 A1, specifically at Paragraph [0063]. The entire disclosure of this publication, and specifically the cited paragraph, is incorporated by reference herein.

In one embodiment, disclosed herein are methods of treating cancer in a subject by providing a composition comprising a tumor targeted corrole nanoparticle, and administering a therapeutically effective dosage of the composition to the subject, in another embodiment, the tumor targeted corrole nanoparticle includes manganese (Mn), iron (Fe), and/or gallium (Ga). In another embodiment, the nanoparticle is the combination of a corrole compound with a HerPBK10 molecule. In another embodiment, the nanoparticle is HerMn, HerFe, or HerGa.

In another embodiment, disclosed herein are methods of imaging cancer in a subject by providing a composition comprising a tumor targeted corrole nanoparticle, and administering an effective dosage of the composition to the subject. In another embodiment, the tumor targeted corrole nanoparticle includes manganese (Mn), iron (Fe), and/or gallium (Ga). In another embodiment, the nanoparticle is the combination of a corrole compound with a HerPBK10 molecule. In another embodiment, the nanoparticle is HerMn, HerFe, or HerGa. In another embodiment, the imaging is performed by MRI.

In another embodiment, disclosed herein are methods of imaging and diagnosing a disease in a subject by providing a composition comprising a targeted corrole nanoparticle, administering an effective dosage of the composition to the subject, and diagnosing the disease based on imaging of the subject. In another embodiment, the targeted corrole nanoparticle includes manganese (Mn), iron (Fe), and/or gallium (Ga). In another embodiment, the nanoparticle is the combination of a corrole compound with a HerPBK10 molecule. In another embodiment, the nanoparticle is HerMn, HerFe, or HerGa. In another embodiment, the imaging is performed by MRI.

In another embodiment, disclosed herein are methods of imaging and treating a disease in a subject by providing a composition comprising a targeted corrole nanoparticle, administering an effective dosage of the composition to the subject, and imaging and treating the subject. In another embodiment, the targeted corrole nanoparticle includes manganese (Mn), iron (Fe), and/or gallium (Ga). In another embodiment, the nanoparticle is the combination of a corrole compound with a HerPBK10 molecule. In another embodiment, the nanoparticle is HerMn, HerFe, or HerGa. In another embodiment, the imaging is performed by MRI.

In one embodiment, disclosed herein are compositions comprising a targeted corrole nanoparticle. In another embodiment, the targeted corrole nanoparticle includes manganese (Mn), iron (Fe), and/or gallium (Ga). In another embodiment, the nanoparticle is the combination of a corrole compound with a HerPBK10 molecule. In another embodiment, the nanoparticle is HerMn, HerFe, or HerGa. In another embodiment, the imaging is performed by MRI.

In various embodiments, disclosed herein are pharmaceutical compositions including a pharmaceutically acceptable excipient along with a therapeutically effective amount of a targeted corrole nanoparticle. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions disclosed herein can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins Pa., USA) (2000).

Typical dosages of an effective targeted corrole nanoparticle can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal. models, as previously described.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not :limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Mn-Corrole Shows Highest T1 Relaxation Time In Vitro

The inventors assessed an initial panel of corroles to determine which, if any, exhibit potential as a contrast agent for MRI To determine this, the inventors measured the T1 time reduction of each at increasing concentrations, under in vitro conditions. Of the three corroles measured (gallium, iron, and manganese—metallated compounds), the Mn corrole, S2Mn, exhibited the largest T1 time shortening (FIG. 1). Subsequent studies were therefore performed using this compound.

Example 2

Targeted Mn-Corrole, FlerMn, Kills Tumors In Vivo

Figure 2:
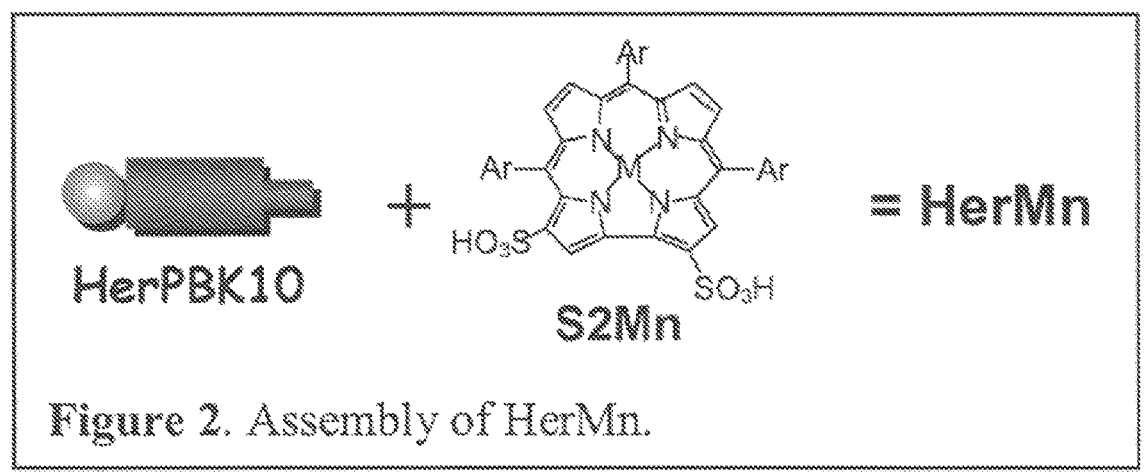
FIG. 2 depicts, in accordance with an embodiment herein, assembly of HerMn.
Figure 3:
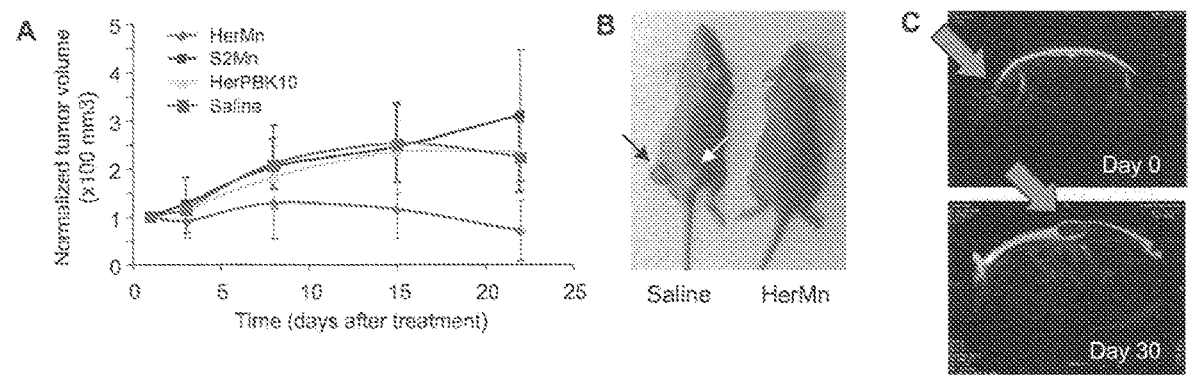
FIG. 3 depicts, in accordance with an embodiment herein, tumor-toxicity of HerMn. HerMn was injected (5 nmoles per injection) into the tail vein of female nude mice bearing bilateral flank tumors of human HER2+ cancer cells. Mice received daily injections, 1 x/day for 7 days, while tumors were monitored for growth by measuring volumes using calipers on a regular basis. Control injections included equivalent doses of untargeted corrole (S2Mn), HerPBK10, and vehicle alone (saline). A, Growth plots of tumor volumes from treated mice. N=6-8 tumors per sample. B, Mice treated with saline (left mouse) or HerMn (right mouse). Arrows point to tumors. C, MRI of tumor from HerMn-treated mouse on the day of the last injection (Day 0) and 30 days later (Day 30). Tumor is indicated by the arrow. The MRI shows tumor volume without the use of a contrast agent.

The inventors examined whether S2Mn was toxic to tumors when delivered by the targeting protein, HerPBK10. The particle resulting from the non-covalent interaction between S2Mn and HerPBK10 (called HerMn; FIG. 2) was tested for tumor-targeted toxicity in an in vivo xenograft mouse model of human HER2+ cancer. We delivered HerMn at 5 nmoles per injection or the equivalent dose of S2Mn alone, HerPB10 alone, and saline, via tail vein injection daily for 7 days, and monitored tumor growth for 25 days following the final injection. This study showed that HerMn can cause tumor growth ablation in vivo whereas the individual components do not (FIG. 3).

Example 3

S2Mn Exhibits T1 Time Shortening and MRI Contrast In Vivo

Figure 4:
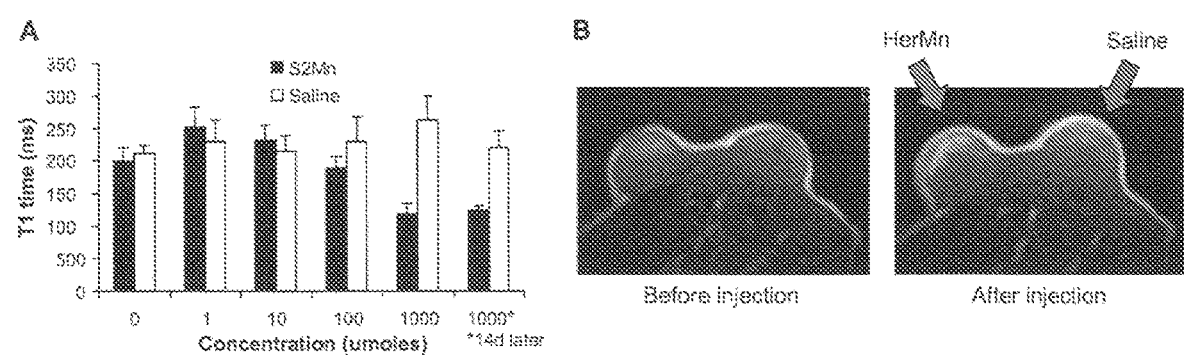
FIG. 4 depicts, in accordance with an embodiment herein, T1 time reduction and MRI contrast of S2Mn in vivo. Female nude mice bearing bilateral flank xenografts of human HER2+ tumors received intratumoral injections of S2Mn or saline at the indicated doses. A, T1 relaxation time measurements obtained from the tumors of live mice. B, MRI of tumors in live mice before (left image) and after (right image) injections of either HerMn (1 mmole) or saline (indicated by left and right arrows, respectively).

To determine whether S2Mn exhibited contrast by MRI, the inventors measured the T1 time shortening of S2Mn in vivo after intratumoral injection at different doses per injection. An accumulation of 100 umoles S2Mn in the tumor yielded a significant difference in T1 time shortening compared to the equivalent volume of saline injected into the contralateral tumor (FIG. 4A). However, 1 mmole S2Mn produced a better T1 time reduction that could be better distinguished from background tissue signals (FIG. 4A), and likewise yielded a detectable contrast by MRI (FIG. 4B).

Taken altogether, the findings demonstrate that HerMn is a viable agent for both targeted tumor killing and detection via MRI. These findings support translation of HerMn toward future clinical application.

Example 4

Overview

As disclosed herein, the inventors developed a tumor-targeted protein-based nanoparticle capable of simultaneous tumor detection and treatment. In one embodiment, the nanoparticle is formed by noncovalent assembly of a recombinant tumor-targeted cell penetration protein (HerPBK10) with water-soluble sulfonated corroles, forming round virus-like particles of 10-20 nm diameter. While HerPBK10 facilitates tumor targeting and cell membrane penetration, the corrole noncovalently binds to the protein and enables detection and cytotoxicity. The inventors demonstrated that that delivery of a gallium-metallated corrole by HerPBK10 (resulting in the complex, HerGa) can emit an intense red fluorescence to track tumor-targeting while selectively killing HER2+ tumors. However, tumor detection using HerGa is only allowed when tumors are localized within several centimeters under the skin since the penetration depths of light are limited to several centimeters. Thus, the usage of HerGa for tumor detection in the clinic may require more advanced imaging methodologies including endoscopic technologies. As disclosed herein, the inventors have explored whether alternative metallated corroles can be used that, when combined with HerPBK10, are as cytotoxic as HerGa but bear sufficient contrast properties to enable detection using clinically relevant devices such as MRI. The inventors examined whether tumor-targeted particles carrying manganese (Mn) and iron (Fe) corroles (HerMn or HerFe, respectively) bear sufficient contrast for MRI while sustaining targeted-toxicity to HER2+ tumor cells in vivo.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of imaging a condition in a subject using magnetic resonance imaging (MRI), comprising:
   a) administering to the subject an effective amount of a composition comprising a targeted nanoparticle, wherein the targeted nanoparticle comprises a targeting polypeptide and a corrole, wherein the corrole comprises iron (Fe), and wherein the targeting polypeptide comprises a Her segment and a penton base segment; and
   b) imaging the condition in the subject by MRI.

2. The method of claim 1, wherein the polypeptide is a HerPBK10 molecule.

3. The method of claim 1, wherein the nanoparticle is HerFe.

4. The method of claim 1, wherein the condition is cancer.

5. The method of claim 1, wherein the corrole is

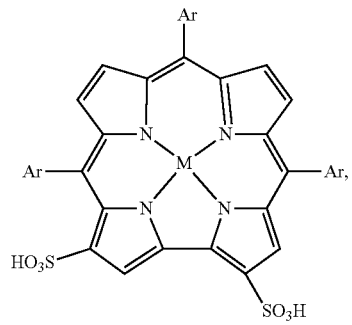

wherein M is iron (Fe).

6. The method of claim 1, wherein the corrole is a sulfonated corrole.

7. A method of treating a cancer in a subject, comprising:
   administering to the subject a therapeutically effective dosage of a composition comprising a tumor-targeted nanoparticle, wherein the tumor-targeted nanoparticle comprises a tumor-targeting polypeptide and a corrole, thereby reducing the size of the cancer;
   wherein the corrole comprises iron (Fe); and
   wherein the tumor-targeting polypeptide comprises a Her segment and a penton base segment.

8. The method of claim 7, wherein the polypeptide is a HerPBK10 molecule.

9. The method of claim 7, wherein the nanoparticle is HerFe.

10. The method of claim 7, wherein the corrole is

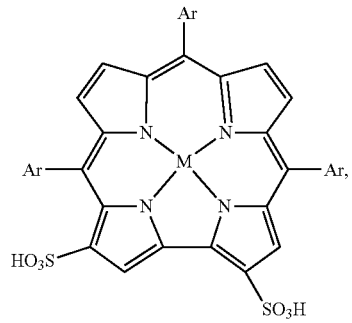

wherein M is iron (Fe).

11. The method of claim 7, wherein the corrole is a sulfonated corrole.

12. The method of claim 7, further comprising imaging the cancer using magnetic resonance imaging (MRI).

* * * * *